US011751967B2

(12) United States Patent
Brasset et al.

(10) Patent No.: US 11,751,967 B2
(45) Date of Patent: Sep. 12, 2023

(54) FINGERS-DRIVEN HAPTIC INTERFACE FOR ROBOT-ASSISTED SURGICAL SYSTEM

(71) Applicant: Asensus Surigal US, Inc., Durham, NC (US)

(72) Inventors: Damien Brasset, Milan (IT); Stefano Maghini, Vimodrone (IT); Riccardo Pozzato, Voghera (IT)

(73) Assignee: Asensus Surgical US, Inc., Durham, NC (US)

( * ) Notice: Subject to any disclaimer, the term of this patent is extended or adjusted under 35 U.S.C. 154(b) by 317 days.

(21) Appl. No.: 16/931,442

(22) Filed: Jul. 16, 2020

(65) Prior Publication Data
US 2021/0038332 A1 Feb. 11, 2021

Related U.S. Application Data

(60) Provisional application No. 62/874,979, filed on Jul. 16, 2019.

(51) Int. Cl.
*G09G 5/00* (2006.01)
*A61B 34/00* (2016.01)
*A61B 34/35* (2016.01)
*A61B 34/20* (2016.01)

(52) U.S. Cl.
CPC .............. *A61B 34/76* (2016.02); *A61B 34/20* (2016.02); *A61B 34/25* (2016.02); *A61B 34/35* (2016.02); *A61B 34/74* (2016.02); *A61B 2034/2048* (2016.02); *A61B 2034/741* (2016.02)

(58) Field of Classification Search
CPC ........... A61B 2017/00203; A61B 2017/00216; A61B 2017/00438; A61B 2017/00539; A61B 2017/00973; A61B 2034/2048; A61B 2034/741; A61B 34/20; A61B 34/25; A61B 34/30; A61B 34/35; A61B 34/74; A61B 34/76; A61B 90/361
See application file for complete search history.

(56) References Cited

U.S. PATENT DOCUMENTS

| 5,004,391 A | 4/1991 | Burdea |
| 2014/0215684 A1* | 8/2014 | Hardy ................... G06F 3/014 2/160 |
| 2016/0296838 A1 | 10/2016 | Goetgeluk et al. |
| 2018/0196515 A1* | 7/2018 | Appleyard ............. G06F 3/016 |
| 2018/0243626 A1* | 8/2018 | Bonutti ................. A61B 34/74 |
| 2019/0083187 A1* | 3/2019 | Danitz ................. A61N 1/0502 |

* cited by examiner

*Primary Examiner* — Insa Sadio

(57) ABSTRACT

A haptic interface for a robot-assisted surgical system makes use of a plurality of sensors and a plurality of bladders each mountable to fingers a human hand. A processor receives user input from the sensors in response to movement of the fingers and, in response to the input, causing movement or actuation of a surgical instrument on a robotic manipulator. The processor also receives force input from force sensors of the surgical system corresponding to forces against the surgical instrument, and in response to the force input causing fluid to move into one or more of the bladders.

9 Claims, 4 Drawing Sheets

FINGERS-DRIVEN HAPTIC INTERFACE FOR ROBOT-ASSISTED SURGICAL SYSTEM

This application claims the benefit of U.S. Provisional Application No. 62/874,979, filed Jul. 16, 2019.

BACKGROUND

Surgical robotic systems are typically comprised of one or more robotic manipulators and a user interface. The robotic manipulators carry surgical instruments or devices used for the surgical procedure. A typical user interface includes input devices, or handles, manually moveable by the surgeon to control movement of the surgical instruments carried by the robotic manipulators. The surgeon uses the interface to provide inputs into the system and the system processes that information to develop output commands for the robotic manipulator.

The ability to understand the forces that are being applied to the patient by the robotically controlled surgical devices during minimally invasive surgery is advantageous to the surgeon. Communication of information representing such forces to the surgeon via the surgeon interface is referred to as "haptic feedback." In some systems, haptic feedback is communicated to the surgeon in the form of forces applied by motors to the surgeon interface, so that as the surgeon moves the handles of the surgeon interface, s/he feels resistance against movement representing the direction and magnitude of forces experienced by the robotically controlled surgical device. Forces represented can include both the forces at the tips of the robotically controlled devices and/or the forces being applied by the shaft of the robotically controlled device to the trocar at the entrance point to the body, giving the surgeon complete understanding of the forces applied to the device so s/he can better control the device during surgery.

The present application describes a haptic user input device that is worn on the hand and that generates input to the system via articular of the user's fingers and that communicates haptic feedback to the user using inflatable bladders positioned on the user's fingers.

DETAILED DESCRIPTION

Figure 1:
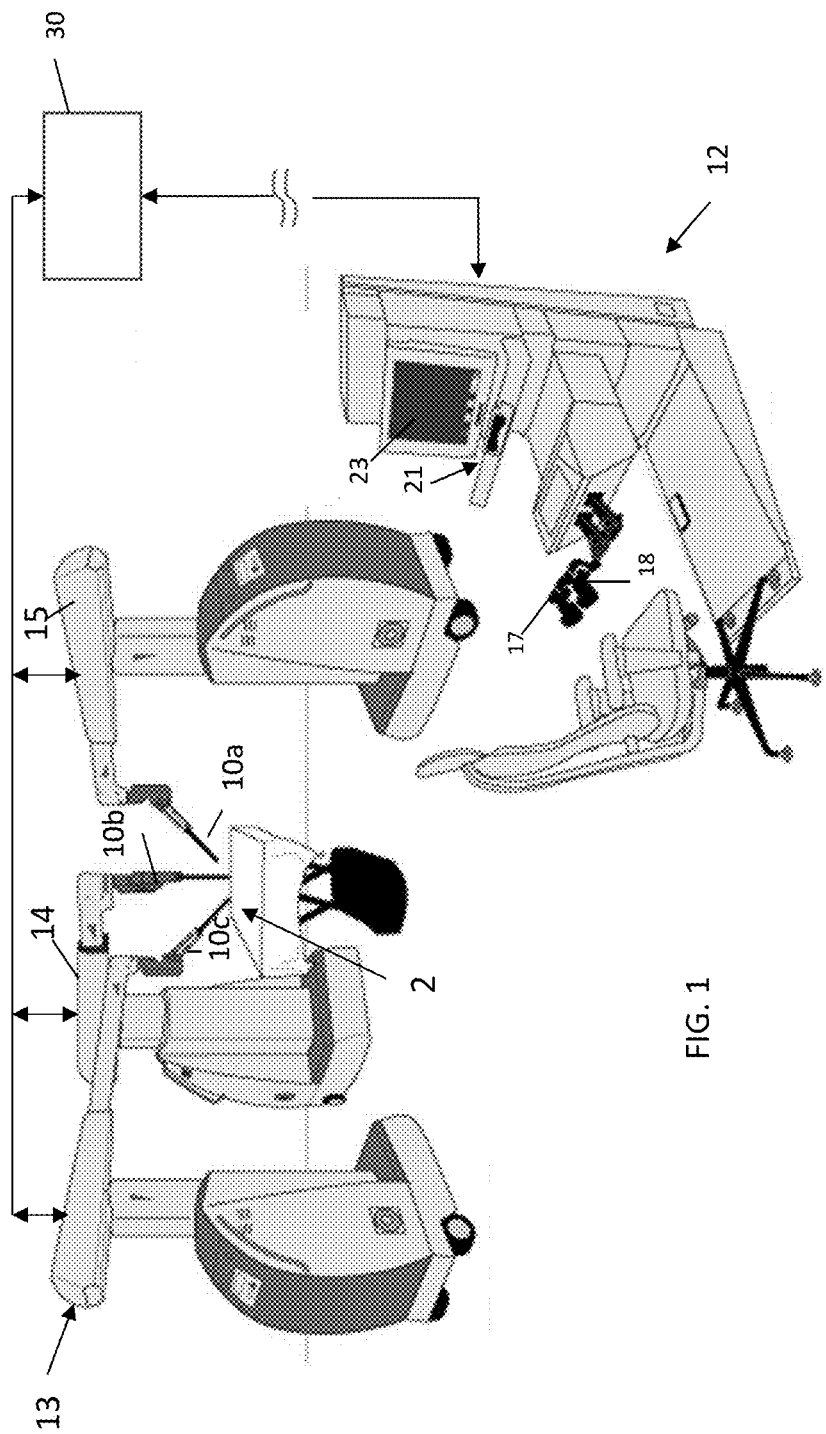
FIG. 1 shows an example of a robot-assisted surgical system.

This application describes a haptic user interface for a robot-assisted surgical system. Although the inventions described herein may be used on a variety of robotic surgical systems, the embodiments will be described with reference to a system of the type shown in FIG. 1.

In the illustrated system, a surgeon console 12 has two input devices such as the new haptic interface described below, and/or handles 17, 18. The new haptic interface described below may be provided in lieu of, or in addition to, the handles 17, 18. Where both types are provided, the user might choose to utilize the more conventional user input devices 17, 18 to give input when performing certain surgical tasks, and to use the new haptic interface for other surgical tasks.

The input devices are configured to be manipulated by a user to generate signals that are used to command motion of a robotically controlled device in multiple degrees of freedom. In use, the user selectively assigns the two input devices to two of the robotic manipulators 13, 14, 15, allowing surgeon control of two of the surgical instruments 10a, 10b, and 10c disposed at the working site at any given time. To control a third one of the instruments disposed at the working site, one of the two input devices is operatively disengaged from one of the initial two instruments and then operatively paired with the third instrument. A fourth robotic manipulator, not shown in FIG. 1, may be optionally provided to support and maneuver an additional instrument.

One of the instruments 10a, 10b, 10c is a camera that captures images of the operative field in the body cavity. The camera may be moved by its corresponding robotic manipulator using input from a variety of types of input devices, including, without limitation, one of the new haptic interface devices, the handles 17, 18, additional controls on the console, a foot pedal, an eye tracker 21, voice controller, etc. The console may also include a display or monitor 23 configured to display the images captured by the camera, and for optionally displaying system information, patient information, etc.

A control unit 30 is operationally connected to the robotic arms and to the user interface. The control unit receives user input from the input devices corresponding to the desired movement of the surgical instruments, and the robotic arms are caused to manipulate the surgical instruments accordingly.

The input devices are configured to be manipulated by a user to generate signals that are processed by the system to generate instructions used to command motion of the manipulators in order to move the instruments in multiple degrees of freedom.

Where handles 17, 18 are used in addition to the new haptic interface devices, one or more of the degrees of freedom of the handles may be coupled with an electromechanical system capable of providing gravity compensation for the user input, and/or providing haptic feedback to the surgeon.

The surgical system allows the operating room staff to remove and replace surgical instruments carried by the robotic manipulator, based on the surgical need. Once instruments have been installed on the manipulators, the surgeon moves the input devices to provide inputs into the system, and the system processes that information to develop output commands for the robotic manipulator in order to move the instruments and, as appropriate, operate the instrument end effectors.

New Fingers-Driven Haptic Interface

Figure 2:
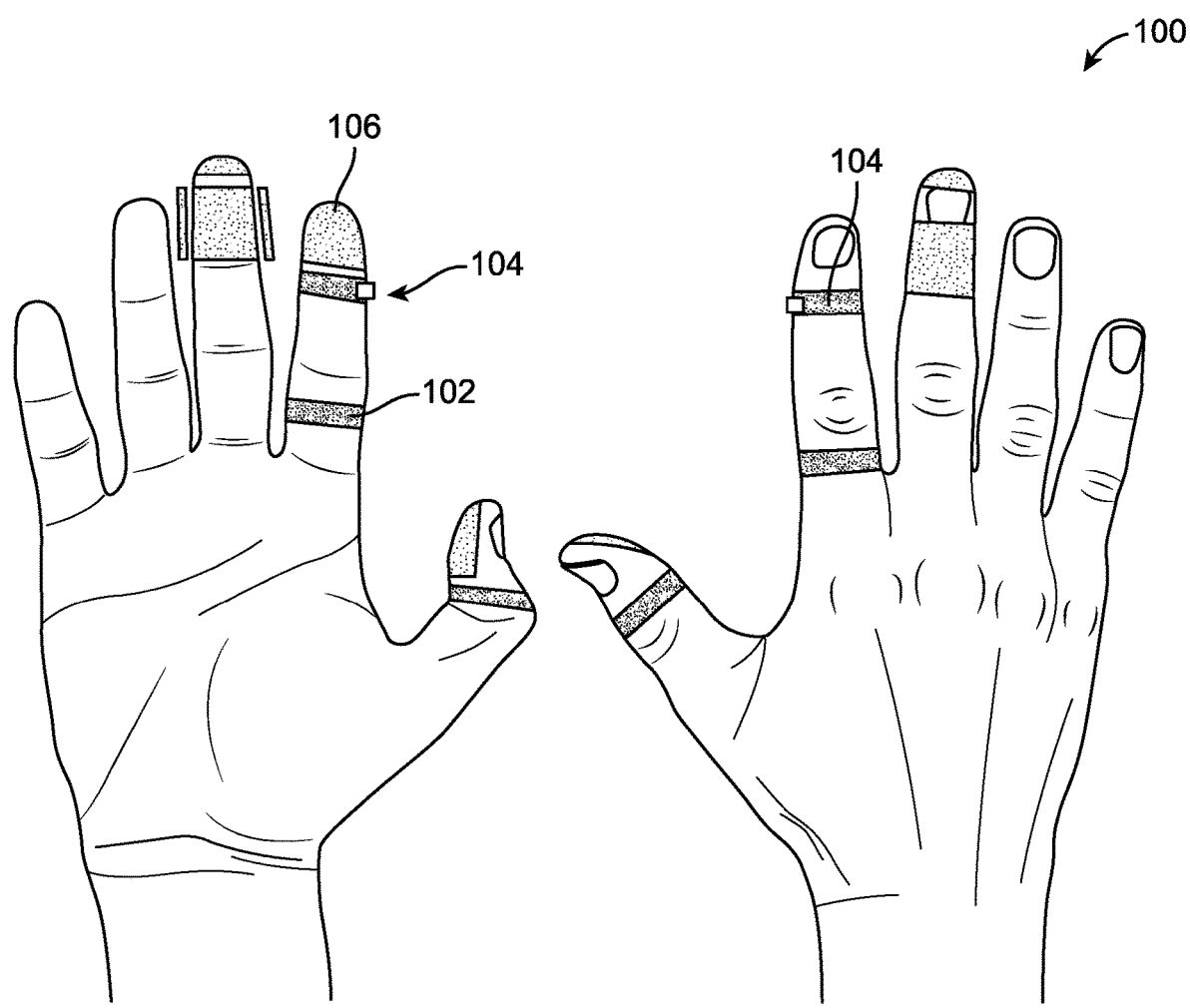
FIG. 2 illustrates components of a first embodiment of a haptic user interface.

FIG. 2 schematically illustrates an embodiment of a fingers-driven haptic interface 100. Each interface 100 is worn on a hand of a user, and includes acceleration and angular velocity sensors 102, (each of which may be an IMU, or separate accelerometer and a gyroscope components; for simplicity here the term IMU is used to connote either configuration) to generate signals in response to movement of a digit of the user's hand, an input switch 104 such as a push button, sliding switch, touch sensitive surface, joystick, etc. allowing the user to cause an input signal to be delivered to the system, The interface further includes bladders 106. The bladders are designed to be filled with gas or other fluid to activate pressure that simulates touch. As such they are fluidly coupled to a gas or fluid source, which may be one or more neighboring bladders containing the gas/fluid source. Additionally, an electromechanical actuation system or pump is provided to drive the fluid into the relevant haptic bladder of the user interface device when the processor causes it to do so in order to do so in order to give haptic feedback to the user.

The arrangement of these components that is illustrated in FIG. 2 will next be described. It should be understood, however, that in alternative embodiments different number and positions for these components may be used.

In the configuration illustrated in FIG. 2, there is an IMU for one phalanx of the thumb, and IMU's on each of two phalanx's for the index finger. While not shown in FIG. 2, two additional IMU's may be positioned on the middle finger, one on each phalanx. The switch 104 is preferably positioned on the index finger so that the thumb may be used to activate/engage it. As shown, the switch may be included on the IMU for that finger.

In the illustrated configuration, the haptic interface positions bladders 106 on each of the thumb, index finger and middle finger as represented in FIG. 2. More specifically, bladders 106 are positioned to contact the pads of these fingers. In one configuration, the thumb and index finger each include one such bladder, and the system is programmed to deliver force feedback to the index finger and thumb by inflating one or both of these bladders when the end effector of the surgical instrument is closed into contact with tissue, a needle, or another instrument or material used in the surgical procedure.

The haptic interface of the FIG. 2 configuration utilizes five bladders positioned on the middle finger. These bladders are positioned on the user's hand to deliver force feedback to the user along three axes of motion of the surgical instrument as it is used during the surgical procedure. One pair of bladders, which generates force feedback corresponding to forces experienced by the surgical instrument along the pitch axes, is positioned with one bladder on the pad of the finger and one bladder on the back of the finger. A second pair of bladders, which generates force feedback corresponding to forces experienced by the surgical instrument along the yaw axis, are positioned on the sides of the middle finger. The fifth bladder, which generates force feedback along the instrument's insertion axis (along its longitudinal axis), is disposed at the tip of the finger.

Figure 3:
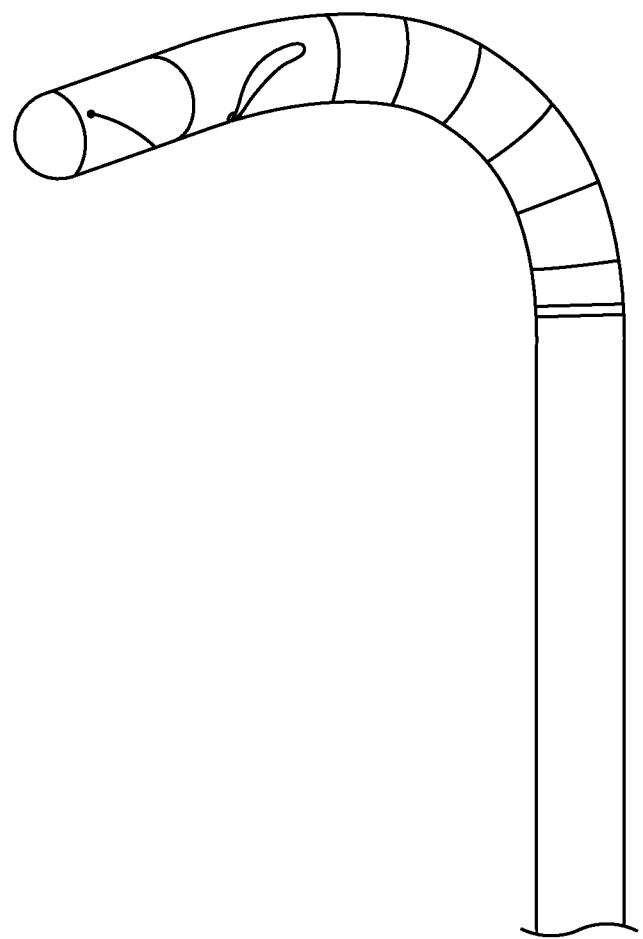
FIG. 3 shows a surgical instrument in a curved configuration.

The arrangement of IMUs may be used to generate signals used by a process of the surgical system to control electromechanical motion of a surgical instrument held by a robotic manipulator. For example, movement of the thumb and index finger towards/away from one another may be mapped to motion closing the jaws of the surgical instrument. Motion to move the user's hand in pitch and jaw directions (relative to the user's wrist) may be used to move the instrument in pitch and yaw. Forward/rearward motion of the user's arm along the axis of the user's forearm may be mapped to movement of the instrument along the insertion axis, and bending motion of the middle finger or forefinger may be mapped to bending (as shown in FIG. 3) or articulation of the bending or articulating portion of a surgical instrument.

The IMUs, bladders etc. may be mounted to the user's hand in a number of ways. In one embodiment, the IMUs are worn as rings on the identified digits, and the switch is positioned on one of the rings. Bladders are disposed in sleeves placed over the fingertips. In another embodiment, a hand-mounted device is provided that has the IMUs mounted to it at the corresponding phalanxes, and the bladders and button mounted to it to contact the fingers at locations such as those shown in FIG. 2.

The components of the haptic interface are in wired or wireless communication with a control system, as discussed above in the description of the surgical robotic system.

Note that while IMUs are described as the sensors for measuring hand motion, other sensors might be used instead of, or in combination, with the IMUs.

For example, a hand-mounted haptic interface may include articulating linkages that track motion of the relevant fingers, and sensors that measure movement of the linkages. In this embodiment, input for some degrees of freedom or actions of the instrument might come from such sensors (e.g. instrument articulation, jaw open-close), while others (axial roll, pitch and yaw) might come from IMUs.

Figure 4:
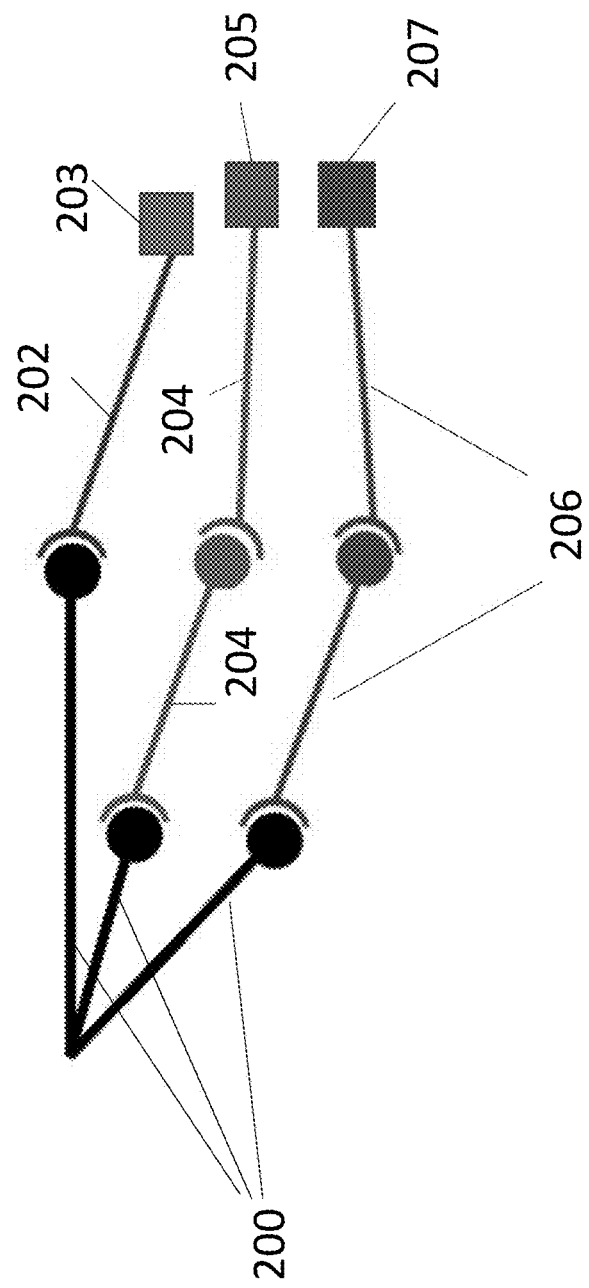
FIG. 4 schematically illustrates degrees of freedom of finger motion that may be used to give input using a fingers-driven haptic interface of the type described herein, and further illustrates positioning of the haptic bladders relative to the degrees of freedom.

FIG. 4 schematically represents articulation degrees of freedom corresponding to thumb, index, and middle fingers of a human hand that may be used to generate input using the second type of haptic interface device described here. In this drawing, the proximal lines 200 represent fixed members. Line 202 represents the single articulation of the thumb portion, and thumb bladder 203 is disposed at the tip of the thumb. Lines 204 represent the two articulations of the index finger portion and include bladder 205 at the distal end. Lines 206 represent the two articulations of the middle finger portion and have at their end the bladders 207 (which may be the arrangement of five bladders described above).

We claim:

1. A haptic interface for a robot-assisted surgical system that includes a manipulator, a surgical instrument on the manipulator, and one or more forces sensors positioned to detect forces against the surgical instrument, the haptic interface comprising:
   a plurality of sensors mountable to a human hand, wherein the plurality of sensors includes a plurality of accelerators, gyroscopes, or IMUs;
   a plurality of bladders mountable to fingers of the human hand;
   at least one processor and at least one memory, the at least one memory storing instructions executable by said at least one processor to:
   receive user input from the sensors in response to movement of the fingers and, in response to the input, causing movement or actuation of a surgical instrument,
   receive force input from force sensors of the surgical system corresponding to forces against the surgical instrument, and, in response to the force input causing fluid to move into one or more of the bladders to provide tactile feedback to the human hand corresponding to the forces against the surgical instrument.

2. The system of claim 1, wherein the haptic interface further includes a plurality of linkages including joints, the linkages moveable relative to the joints in response to articulating of a corresponding finger, and wherein the plurality of sensors includes sensors positioned to measure movement of linkages.

3. The system of claim 1, wherein the instructions are executable by the processor to cause movement of the surgical instrument in at least one of the following: pitch, roll, yaw, articulation or bending, jaw actuation, insertion axis motion.

4. The system of claim 1, wherein the plurality of sensors includes first and second IMUs, the first IMU mountable on an index finger of a user and the second IMU mountable on mountable to a thumb of the user, wherein the instructions are executable by said at least one processor to close jaws of the surgical instrument in response to relative movement of the index finger towards the thumb detected by the first or second IMU.

5. The system of claim 4, wherein the instructions are further executable by said at least one processor to close jaws of the surgical instrument in response to relative movement of the index finger away from the thumb detected by the first or second IMU.

6. The system of claim 1, wherein the instructions are executable by said at least one processor to move the surgical instrument in pitch or yaw in response to movement of the users hand in pitch or yaw relative to the wrist as detected by at least one of the plurality of sensors.

7. The system of claim 1, wherein the instructions are executable by said at least one processor to bend or articulate the surgical instrument in response to bending movement of a finger as detected by at least one of the plurality of sensors.

8. The system of claim 1, wherein the instructions are executable by said at least one processor to move the surgical instrument along its insertion axis in response to movement of the user's forearm along its axis as detected by at least one of the plurality of sensors.

9. A haptic interface for a robot-assisted surgical system that includes a manipulator, a surgical instrument on the manipulator, and one or more forces sensors positioned to detect forces against the surgical instrument, the haptic interface comprising:

a plurality of linkages positionable on fingers of a human hand, the linkages including joints, the linkages moveable relative to the joints in response to articulating of a corresponding finger, and wherein sensors mountable to a human hand, wherein the sensors include a first plurality of sensors positioned to measure movement of linkages, and a second plurality of sensors comprising accelerometers, gyroscopes or IMUs positioned to detect movement of the hand in roll, pitch or yaw;

a plurality of bladders mountable to fingers of the human hand;

at least one processor and at least one memory, the at least one memory storing instructions executable by said at least one processor to:

receive user input from the first plurality of sensors in response to articulation of the linkages resulting from movement of the fingers and, in response to the input, causing movement or actuation of a surgical instrument in jaw actuation or instrument articulation;

receive user input from the second plurality of sensors and, in response to the input, causing movement or actuation of a surgical instrument movement of the surgical instrument in at least one of axial roll, pitch and yaw;

receive force input from force sensors of the surgical system corresponding to forces against the surgical instrument, and in response to the force input causing fluid to move into one or more of the bladders to provide tactile feedback to the human hand corresponding to the forces against the surgical instrument.

* * * * *